(12) United States Patent
Zheng et al.

(10) Patent No.: US 10,449,167 B2
(45) Date of Patent: Oct. 22, 2019

(54) POLYAMINE DERIVATIVE MEDICINAL SALT AND PREPARATION METHOD AND USE

(71) Applicant: Chongqing Antixin Biotechnology Co. Ltd., Chongqing (CN)

(72) Inventors: Yue Zheng, Chongqing (CN); Jun Deng, Chongqing (CN); Qingguang Liu, Chongqing (CN)

(73) Assignee: Chongqing Antixin Biotechnology Co., LTD., Chongqing (CN)

( * ) Notice: Subject to any disclaimer, the term of this patent is extended or adjusted under 35 U.S.C. 154(b) by 0 days.

(21) Appl. No.: 15/770,833

(22) PCT Filed: Oct. 28, 2016

(86) PCT No.: PCT/CN2016/103693
§ 371 (c)(1),
(2) Date: Apr. 25, 2018

(87) PCT Pub. No.: WO2017/071629
PCT Pub. Date: May 4, 2017

(65) Prior Publication Data
US 2018/0338934 A1  Nov. 29, 2018

(30) Foreign Application Priority Data
Oct. 29, 2015 (CN) .......................... 2015 1 0729318

(51) Int. Cl.
*A61K 31/165* (2006.01)
*C07C 237/42* (2006.01)

(52) U.S. Cl.
CPC .......... *A61K 31/165* (2013.01); *C07C 237/42* (2013.01)

(58) Field of Classification Search
CPC .. A61K 31/165; C07C 233/40; C07C 235/34; C07C 237/42
USPC ........................................................ 514/617
See application file for complete search history.

(56) References Cited

FOREIGN PATENT DOCUMENTS

CN    102267922 A    12/2011

OTHER PUBLICATIONS

Alain, T. et al. "Parameters Influencing the Release of Tertiary Alcohols from the Surface of 'Spherical' Dendrimers and 'Linear' Stylomers by Neighbouring-Group-Assisted Hydrolysis of 2-Carbamoylbenzoates." Chemistry: a European Journal, vol. 15, Issue12, Mar. 9, 2009, pp. 2846-2860.

*Primary Examiner* — Kristin A Vajda
(74) *Attorney, Agent, or Firm* — Burns & Levinson LLP; Janine M. Susan; Marlo Schepper Grolnic (57) ABSTRACT

The invention relates to a kind of medicinal salts of polyamine derivatives, preparation method and use thereof in preparation of a drug for treating sepsis. These novel compounds have good antagonistic action on a plurality of pathogen-associated molecular patterns that induce sepsis, such as bacterial lipopolysaccharide (endotoxin), bacterial genomic DNA, peptidoglycan, lipoteichoic acid, virus RNA, and zymosan, and can be used for preparation of a drug for treating sepsis.

9 Claims, 5 Drawing Sheets

POLYAMINE DERIVATIVE MEDICINAL SALT AND PREPARATION METHOD AND USE

CROSS-REFERENCE TO RELATED APPLICATIONS

This application is the U.S. national phase entry under 35 U.S.C. § 371 of International Application No. PCT/CN2016/103693, filed Oct. 28, 2016, entitled POLYAMINE DERIVATIVE MEDICINAL SALT AND PREPARATION METHOD AND USE, which in turn claims priority to and benefit of Chinese Application No. 201510729318.8, filed Oct. 29, 2015, the contents of which are incorporated herein by reference in their entirety for all purposes.

FIELD

The present invention relates to the field of medical technology, and particularly relates to the medicinal salts of polyamine derivatives and their preparation methods and use in preparation of drugs for treating sepsis.

BACKGROUND

Sepsis is a systemic inflammatory response syndrome (systemic inflammatory response syndrome, SIRS) caused by infection, the number of patients in the globe every year reached up to 19,000,000. Although current antibiotics and critical medical technology had been made significant development, sepsis is still a major factor of the death of infected patients, and there is no ideal treatment so far.

Research shows that the mechanism of sepsis is that the pathogen-associated molecular pattern (PAMP) released by pathogens such as bacteria, virus, fungus etc. is identified by a pattern recognition receptor (PRR) of host natural immune system, then activated the inflammatory cells, thereby triggering systemic excessive inflammatory response. Epidemiology survey shows that the PAMP that triggers sepsis mainly include lipopolysaccharide (LPS), bacterial genomic DNA (CpG DNA), peptidoglycan (PGN), lipoteichoic acid (LTA), virus RNA and zymosan. Research of American scholar Diptesh Sil et al shows a synthetic polyamines named DS-96 has antagonistic effect on LPS (Sil D, Shrestha A, Kimbrell M R, Nguyen T B, Adisechan A K, Balakrishna R, Abbo B G, Malladi S, Miller K A, Short S, Cromer J R, Arora S, Datta A, David S A. Bound to shock: protection from lethal endotoxemic shock by a novel, nontoxic, alkylpolyamine lipopolysaccharide sequestrant. Antimicrobial agents and chemotherapy. 2007; 51(8): 2811-2819.). Tony Velkov et al report polymyxin antibiotics having vast free amino groups has activity to directly antagonize LPS (Velkov T, Thompson P E, Nation R L, Li J. Structure-activity relationships of polymyxin antibiotics. Journal of medicinal chemistry. 2010; 53(5): 1898-1916.). Chinese invention patent CN102267922B disclosed a polyamine compounds having good antagonistic effect on LPS and CpG DNA.

As previously mentioned, the PAMP as pathogenic factor that triggers sepsis has numerous sources and varieties, but all of drugs so far discovered only antagonize one or several PAMP, it may be difficult to cure sepsis comprehensively and effectively. So it is of important significance to find a drug that can antagonize more PAMP at the same time.

SUMMARY

The purpose of the present invention is to provide a kind of medicinal salts of polyamine derivatives, the medicinal salts of polyamine derivatives can effectively antagonize various PAMP such as LPS, CpG DNA, PGN, LTA, virus RNA and zymosan or the like at the same time, which provides a new therapy for curing sepsis.

The technical solution for the first purpose is:

The medicinal salts of polyamine derivatives are provided, the medicinal salts are salts formed with polyamine derivatives shown in general formula 1 and pharmaceutically acceptable acids through chemical combination, the polyamine derivatives have structure of general formula 1.

1

Wherein, $R_1$~$R_5$ were selected from H or OH or $OCH_3$; $n_1$~$n_5$ were any integer between 0~10. The preferred value of $n_1$~$n_4$ were any integer between 1~10; the preferred value of $n_5$ was any integer between 0~10.

The pharmaceutically acceptable acid is inorganic acid or organic acid.

The inorganic acid is hydrochloric acid, sulfuric acid, phosphoric acid or nitric acid, the preferred is hydrochloric acid or sulfuric acid; the organic acid is acetic acid, oxalic acid, propanedioic acid, succinic acid, benzoic acid, trifluoroacetic acid, maleic acid, fumaric acid, citric acid, tartaric acid, methanesulfonic acid, benzenesulfonic acid, p-Toluene sulfonic acid, the preferred is acetic acid, propanedioic acid, succinic acid, maleic acid, fumaric acid, citric acid, methanesulfonic acid, benzenesulfonic acid or p-Toluene sulfonic acid.

The second purpose of the present invention is to provide a preparation method of the medicinal salts of polyamine derivatives, which the medicinal salts are simple for preparation and has good activity.

The technical solution for the second purpose is:

The preparation method of the medicinal salts of polyamine derivatives has following steps:

Wherein, A is a pharmaceutically acceptable acid.

1) In dichloromethane solution, compound I reacts with protective agent, di-tert-butyl dicarbonate to generate compound II, the equivalent ratio of the compound I and the di-tert-butyl dicarbonate is 1:0.5~2;

2) In a saturated solution of ammonia in methanol, the compound III is generated from compound II through hydrogenation.

3) In ethanol or methanol solution, the compound III reacts with α,β-unsaturated nitrile to generate compound IV, the equivalent ratio of the compound III and a, n-unsaturated nitrile is 1:2~1:3;

4) In a mixed solution of dichloromethane and N,N-Dimethylformamide, compound V reacts with carboxyl activator chlorinated sulfoxide to generate compound VI, the equivalent ratio of the compound V and the carboxyl activator is 1:1~1:2;

5) In a mixed solution of dichloromethane and triethylamine, compound IV reacts with compound VI to generate compound VII, the equivalent ratio of the compound IV and compound VI is 1:2~1:3;

6) In a saturated solution of ammonia in methanol, compound VIII is generated from compound VII through hydrogenation;

7) In methanol solution or a mixed solution of methanol, tetrahydrofuran and water, the medicinal salt of the compound shown in general form 1 is generated from compound VIII through catalytic hydrogenation under the existence of acid, the volume ratio of the methanol, tetrahydrofuran and water is 3:1:1, the equivalent ratio of the compound VIII and acid is 1:1~1:8.

Reaction conditions of step 2) and 6) include using raney nickel corresponding to 10~50% of the mass of compound VII, the pressure is 1~10 Mpa.

Reaction condition of step 7) includes using palladium on carbon corresponding to 10~30% of the mass of the compound VIII, the pressure ranges from atmospheric pressure to 10 Mpa.

The third purpose of the present invention is to provide a use of medicinal salts of polyamine derivatives in preparation of drugs for antagonizing LPS, CpG DNA, PGN, LTA, virus RNA and/or zymosan, and a use of medicinal salts of polyamine derivatives in preparing drug for curing sepsis as well as a use of a pharmaceutical composition comprising the medicinal salts of polyamine derivatives in preparation drugs for treating sepsis.

The polyamine derivative medicinal salt of present invention can be used as activity ingredient and pharmaceutically acceptable carrier and/or diluent, for preparing drugs for curing sepsis.

Above-mentioned drugs, can be administrated through gastrointestinal tract, e.g. through dosage form such as dispersant, tablet, granule, capsule, solution agent, emulsion, suspending agent; or can be administrated parenterally, e.g. through injection, cavity, mucous administration. But generally speaking, polyamine derivatives and their medicinal salts as well as pharmaceutical composition that includes polyamine derivatives and their medicinal salts of present invention adopt parenteral administration, preferably is intravenous administration, most preferably is intravenous infusion. Dosage is 0.1~10 mg per kilogram of body weight of adult every day, dosing frequency is one or more times every day.

The experiment of chemical synthesis shows that the overall yield of the preparation method of the medicinal salts of polyamine derivatives is approximately 20%.

The experiments of pharmacological activity show that polyamine derivatives and their medicinal salts have following pharmacological characteristics:

(1) Good inhibition effect on the release of inflammatory mediators from immune cells induced by LPS, CpG DNA, PGN, LTA, virus RNA and zymosan.

(2) Good inhibition effect on the release of inflammatory mediators from immune cells induced by heat-killed gram negative bacteria (*Escherichia coli*) and gram positive bacteria (*Staphylococcus aureus*).

(3) Significantly improving survival rate of mouse model of sepsis challenged by heat-killed gram negative bacteria (*Escherichia coli*) and gram positive bacteria (*Staphylococcus aureus*).

The polyamine derivatives and their medicinal salts used by the present invention, as compared with drugs that could antagonize a few kinds of PAMP such as LPS or CpG DNA and so on, are distinguished by their antagonistic effect on multiple PAMP, such as LPS, CpG DNA, PGN, LTA, virus RNA and zymosan or the like, and can be used for treating sepsis caused by infection of the gram negative bacteria and gram positive bacteria.

It should understand by those skilled in the art that a variety of acids could be combined with the polyamine derivatives to form salts based on the same principle, in addition to the preferred pharmaceutically acceptable acids of the present invention. Any changes made by those skilled in the art on the implementation of the present disclosure fall within the protection scope of the claims of the present invention.

DESCRIPTION OF THE DRAWINGS

FIGS. 2A-G are the experimental results of the inhibition of polyamine derivative PAM01 hydrochloride on the release of inflammatory mediators from immune cells induced by LPS, CpG DNA, PGN, LTA, virus RNA and zymosan. Wherein

FIGS. 3A and 3B are experimental results of the inhibition of polyamine derivative PAM01 hydrochloride on the release of inflammatory mediators from immune cells induced by heat-killed *Escherichia coli* and *Staphylococcus aureus*. Wherein.

FIGS. 4A and 4B are experimental result of the improvement of polyamine derivative PAM01 hydrochloride in survival rate of mouse model of sepsis. Wherein.

FIGS. 5A-G are experimental results of the inhibition of the sulfate, phosphate, mesylate, benzene sulfonate and acetate of polyamine derivative PAM01 on the release of inflammatory mediators from immune cells induced by LPS, CpG DNA, PGN, LTA, virus RNA and zymosan. Wherein.

FIGS. 6A-G are experimental results of the inhibition of polyamine derivative PAM02~06 hydrochloride on the release of inflammatory mediators from immune cells induced by LPS, CpG DNA, PGN, LTA, virus RNA and zymosan. Wherein.

DETAILED DESCRIPTION

Embodiments are only preferred embodiment to describe the present invention, which do not limit the present invention in any form.

LPS, LTA and zymosan were purchased from Sigma-Aldrich Co. LLC, CpG DNA was purchased from Sangon Biotech (Shanghai) Co. LTD. PGN and virus RNA were purchased from InvivoGen Inc. Other reagents were analytical pure without special description. English abbreviations in embodiments have following meaning.

| abbreviation | meaning | abbreviation | meaning |
| --- | --- | --- | --- |
| DCM | dichloromethane | $SoCl_2$ | Thionyl chloride |
| $Boc_2O$ | di-tert-butyl dicarbonate | $Et_3N$ | triethylamine |

| abbreviation | meaning | abbreviation | meaning |
|---|---|---|---|
| MeOH/NH$_3$ | saturated solution of ammonia in methanol | THF | tetrahydrofuran |
| Raney Ni | Raney nickel | H$_2$O | Water |
| H$_2$ | hydrogen | Pd/C | Palladium on carton |
| MPa | Megapascal | K$_2$CO$_3$ | Potassium carbonate |
| EtOH | Ethanol | BnCl | benzyl chloride |
| DMF | N,N-Dimethylformamide | NaOH | Sodium hydroxide |

| abbreviation | meaning | abbreviation | meaning |
|---|---|---|---|
| LPS | lipopolysaccharide | CpG DNA | bacterial genomic DNA |
| PGN | peptidoglycan | LTA | lipoteichoic acid |
| ssRNA | Single-stranded RNA | dsRNA | Double-stranded RNA |

Embodiment 1: Preparation of Polyamine Derivative PAM01 Hydrochloride 1.1 Experimental Method -continued

PAM01

(1) 6 g of Di (2-cyanoethyl) amine (a) was dissolved in 60 ml of dichloromethane, and di-tert-butyl dicarbonate dissolved in dichloromethane was added dropwise to the solution, after 10 hours of reaction under room temperature, dichloromethane was dried by rotary evaporation, water and ethyl acetate was added for extracting for 3 times (3×20 ml), and the organic layer was dried by anhydrous sodium sulfate, the solution was dried by rotary evaporation to obtain 11.2 g of intermediate b. In high pressure reactor, 11.2 g of intermediate b was dissolved in 400 ml of saturated solution of ammonia in methanol, and 1.2 g of raney nickel was added in the solution then the reactor was filled with hydrogen, and the pressure was 4 MPa, after 72 hours of reaction under room temperature, the reaction solution was filtered by diatomite, and dried by rotary evaporation to obtain 10.4 g of intermediate c. 5.2 g of intermediate c was dissolved into 40 ml of ethanol, and 3.6 ml of acrylonitrile dissolved in ethanol was added dropwise to the solution in ice bath, then the solution was heated up to 40° C. to carry out the reaction for 10 hours, and dried by rotary evaporation to obtain 5.3 g of intermediate d.

(2) 4.2 g of 3,4-Dimethoxyhydrocinnamic acid (e) was dissolved in 20 ml dichloromethane, and 0.1 ml of N,N-Dimethylformamide was added in the solution, then 1.5 ml of thionyl chloride was added, after 5 hours of reaction at 45° C., the solution was dried by rotary evaporation to obtain 3.78 g of intermediate f.

(3) 5.3 g of intermediate d was dissolved in 25 ml of dichloromethane, and 6 ml of triethylamine was added in the solution, 40 ml of intermediate f dissolved into dichloromethane (10%) was added dropwise to the solution at 0° C., after 24 hours of reaction, the solution was concentrated, extracted by diethyl ether, dried by anhydrous sodium sulfate, and dried by rotary evaporation to obtain 7.8 g of intermediate g. In high pressure reactor, 7.8 g of intermediate g was dissolved in 300 ml of saturated solution of ammonia in methanol, and 1 g of raney nickel was added in the solution, then the reactor was filled with hydrogen, and the pressure was 2 MPa, after 72 hours of reaction under room temperature, the reaction solution was filtered by diatomite, and dried by rotary evaporation to obtain 7.2 g of intermediate h. In high pressure reactor, 5 g of intermediate h and 0.6 ml hydrochloric acid were dissolved in 150 ml of a mixed solution of methanol, tetrahydrofuran and water in the ratio 3:1:1 by volume, and 0.5 g of palladium on carbon was added in the solution, then the reactor was filled with hydrogen, and pressure was 10 MPa, after 72 hours of reaction under room temperature, the reaction solution was filtered by diatomite, dried by rotary evaporation, washed by ethyl acetate, and dried under vacuum.

1.2 Experimental result: 2.2 g of polyamine derivative PAM01 hydrochloride was finally obtained, mass spectrum: $[M+H]^+$m/z=630; $^{13}$C NMR spectrum (100 MHz, $D_2O$): δ=176.9, 176.7, 144.7, 144.5, 144.1, 143.9, 127.7, 127.5, 117.9, 117.6, 110.6, 110.4, 110.2, 110.1, 51.7, 51.6, 51.4, 51.2, 50.9, 50.8, 48.5, 48.2, 43.3, 43.2, 41.1, 40.9, 33.7, 33.5, 31.2, 31.0, 27.7, 27.6, 25.2, 25.1 ppm.

Figure 1:
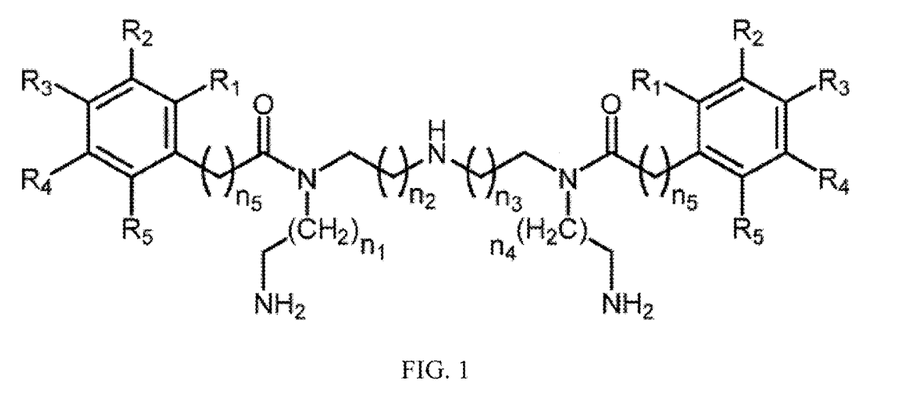
FIG. 1 is general structure formula of polyamine derivatives.

Chemical structure of the polyamine derivative PAM01 was shown in FIG. 1, wherein R is $OCH_3$, $n_1$~$n_4$ are 3, $n_5$ is 2.

Embodiment 2: Preparation of Polyamine Derivative PAM01 Sulfate 2.1 Experimental method: the preparation method of embodiment 1 was employed, reaction was carried out under the same scale and condition, except that hydrochloric acid was replaced by sulfuric acid.

2.2 Experimental result: 1.99 g of polyamine derivative PAM01 sulfate was finally obtained, mass spectrum: $[M+H]^+$m/z=630.

Embodiment 3: Preparation of Polyamine Derivative PAM01 Phosphate 3.1 Experimental method: the preparation method of embodiment 1 was employed, reaction was carried out under the same scale and condition, except that hydrochloric acid was replaced by phosphoric acid.

3.2 Experimental result: 1.85 g of polyamine derivative PAM01 phosphate was finally obtained, mass spectrum: $[M+H]^+$m/z=630.

Embodiment 4: Preparation of Polyamine Derivative PAM01 Mesylate 4.1 Experimental method: the preparation method of embodiment 1 was employed, reaction was carried out under the same scale and condition, except that hydrochloric acid was replaced by methanesulfonic acid.

4.2 Experimental result: 2.32 g of polyamine derivative PAM01 mesylate was finally obtained, mass spectrum: $[M+H]^+$m/z=630.

Embodiment 5: Preparation of Polyamine Derivative PAM01 Benzene Sulfonate 5.1 Experimental method: the preparation method of embodiment 1 was employed, reaction was carried out under the same scale and condition, except that hydrochloric acid was replaced by benzenesulfonic acid.

5.2 Experimental result: 1.83 g of polyamine derivative PAM01 benzene sulfonate was finally obtained, mass spectrum: [M+H]$^+$m/z=630.

Embodiment 6: Preparation of Polyamine Derivative PAM01 Acetate 6.1 Experimental method: the preparation method of embodiment 1 was employed, reaction was carried out under the same scale and condition, except that hydrochloric acid was replaced by acetic acid.

6.2 Experimental result: 1.9 g of polyamine derivative PAM01 acetate was finally obtained, mass spectrum: [M+H]$^+$m/z=630.

Embodiment 7: Preparation of Polyamine Derivative PAM02 Hydrochloride 7.1 Experimental Method:

The preparation method of embodiment 1 was employed, reaction was carried out under the same scale and condition, except that 3,4-Dimethoxyhydrocinnamic acid was replaced by 3-Phenylpropionic acid.

7.2 Experimental result: 1.7 g of polyamine derivative PAM02 hydrochloride was finally obtained, mass spectrum: [M+H]$^+$m/z=510; $^{13}$C NMR spectrum (100 MHz, D$_2$O): δ=176.9, 176.7, 146.5, 146.3, 133.6, 133.5, 133.4, 133.2, 132.7, 132.6, 132.4, 132.3, 131.2, 131.1, 58.6, 58.4, 53.7, 53.5, 51.3, 51.2, 43.5 43.3, 38.4, 38.2, 36.6, 36.4, 33.4, 33.2, 32.2, 32.1 ppm.

Chemical structure of the polyamine derivative PAM02 was shown in FIG. 1, wherein R is H, $n_1$~$n_4$ are 3, $n_5$ is 2.

Embodiment 8: Preparation of Polyamine Derivative PAM03 Hydrochloride 8.1 Experimental Method:

PAM03

The preparation method of embodiment 1 was employed, reaction was carried out under the same scale and condition, except that 3,4-Dimethoxyhydrocinnamic acid was replaced by 3,4-Dihydroxy-benzenepropanoic acid (e), and in the acylating chlorination of 3,4-Dihydroxy-benzenepropanoic acid, 3 g of 3,4-Dihydroxy-benzenepropanoic acid was dissolved into 15 ml of N,N-Dimethylformamide, and 8 g of potassium on carbonate and 6 ml of benzyl chloride were added, after 36 hours of reaction at 80° C., the reaction solution was filtered, extracted by ethyl acetate, washed by saturated salt water, dried by anhydrous sodium sulfate, filtered, and dried by rotary evaporation to obtain 5.6 g of intermediate e2. 5.6 g of intermediate e2 was dissolved in 6 ml of Sodium hydroxide solution (20%), and 6 ml of methanol was added, after 4 hours of reaction at 90° C., the solution was dried by rotary evaporation, then 10 ml of concentrated hydrochloric acid was added in ice bath until it was in strong acidity, solid was precipitated, filtered, and the filter cake was collected to obtain 4.1 g of intermediate e3.

4.1 g of intermediate e3 was dissolved in 20 ml of dichloromethane, and 0.1 ml of N,N-Dimethylformamide was added, then 1.5 ml of thionyl chloride was added in the solution, after 5 hours of reaction at 45° C., the solution was dried by rotary evaporation to obtain intermediate f.

8.2 Experimental result: 2.08 g of polyamine derivative PAM03 hydrochloride was finally obtained, mass spectrum: [M+H]$^+$m/z=574; $^{13}$C NMR spectrum (100 MHz, D$_2$O): δ=176.9, 176.7, 149.8, 149.4, 147.5, 147.6, 138.6, 138.4, 127.9, 127.8, 121.4, 121.2, 119.7, 119.8, 58.6, 58.4, 50.5, 50.4, 48.3, 48.2, 43.2, 43.1, 38.6, 38.4, 36.7, 36.6, 32.9, 32.8, 31.2, 31.1 ppm.

Chemical structure of the polyamine derivative PAM03 was shown in FIG. 1, wherein R is OH, $n_1$~$n_4$ are 3, $n_5$ is 2.

Embodiment 9: Preparation of Polyamine Derivative PAM04 Hydrochloride

9.1 Experimental Method:

(1)

(2)

(3)

g h

PAM04

The preparation method of embodiment 1 was employed, reaction was carried out under the same scale and condition, except that acrylonitrile was replaced by 3-Butene nitrile.

9.2 Experimental result: 2.33 g of polyamine derivative PAM04 hydrochloride was finally obtained, mass spectrum: [M+H]$^+$m/z=658; $^{13}$C NMR spectrum (100 MHz, D$_2$O): δ=176.7, 176.4, 149.7, 149.6, 147.1, 146.9, 132.7, 132.5, 112.7, 112.6, 112.5, 112.3, 122.2, 122.1, 56.6, 56.4, 56.2, 56.1, 49.3, 49.1, 48.8, 48.7, 46.4, 46.2, 41.7, 41.5, 33.2, 33.1, 31.6, 31.4, 27.2, 27.1, 26.7, 26.5, 25.8, 25.7 ppm.

Chemical structure of the polyamine derivative PAM04 was shown in FIG. 1, wherein R is OCH$_3$, $n_1$, $n_2$ are 4, $n_3$ and $n_4$ are 3, $n_5$ is 2.

Embodiment 10: Preparation of Polyamine Derivative PAM05 Hydrochloride

10.1 Experimental Method:

(1)

-continued

The preparation method of embodiment 1 was employed, reaction was carried out under the same scale and condition, except that 3,4-Dimethoxyhydrocinnamic acid was replaced by 3,4-Dimethoxybenzoic acid (e).

10.2 Experimental result: 2.03 g of polyamine derivative PAM05 hydrochloride was finally obtained, mass spectrum: [M+H]'m/z=574; $^{13}$C NMR spectrum (100 MHz, D$_2$O): δ=172.9, 172.7, 146.8, 146.7, 144.6, 144.4, 130.5, 130.4, 111.5, 111.4, 110.6, 110.4, 104.6, 104.5, 54.5, 54.4, 54.2, 54.1, 51.3, 51.2, 52.1, 52.0, 44.3, 44.1, 36.4, 36.3, 24.8, 24.6, 24.1, 24.0 ppm.

Chemical structure of the polyamine derivative PAM05 was shown in FIG. 1, wherein R is OCH$_3$, $n_1$~$n_4$ are 4, $n_5$ is 0.

Embodiment 11: Preparation of Polyamine Derivative PAM06 Hydrochloride 10.1 Experimental Method:

PAM06

The preparation method of embodiment 1 was employed, reaction was carried out under the same scale and condition, except that Di (2-cyanoethyl) amine was replaced by iminodiacetonitrile (a).

10.2 Experimental result: 2.09 g of polyamine derivative PAM05 hydrochloride was finally obtained, mass spectrum: [M+H]$^+$ m/z=602; $^{13}$C NMR spectrum (100 MHz, D$_2$O): δ=176.7, 176.5, 145.8, 145.6, 143.6, 143.4, 130.8, 130.6, 116.6, 116.4, 107.6, 107.4, 105.6, 105.5, 55.6, 55.4, 55.2, 55.1, 50.3, 50.2, 44.2, 44.1, 42.3, 42.1, 34.4, 34.3, 31.2, 31.1, 26.8, 26.6, 22.8, 22.7 ppm.

Chemical structure of the polyamine derivative PAM06 was shown in FIG. 1, wherein R is OCH$_3$, $n_1$ and $n_4$ are 3, $n_2$ and $n_3$ are 2, $n_5$ is 2.

Embodiment 12: Inhibition Effect of Polyamine Derivative PAM01 Hydrochloride on LPS, CpG DNA, PGN, LTA, Virus RNA and Zymosan-Induced Release of Inflammatory Mediators from Immune Cells 12.1 Experimental method: 0.1 ml solutions of LPS (1 µg/ml), CpG DNA (10 µg/ml), PGN (10 µg/ml), LTA (10 µg/ml), virus ssRNA (10 µg/ml), virus dsRNA (10 µg/ml) and zymosan (10 µg/ml) prepared with pyrogen-free water were separately isovolumetrically mixed with 2, 6 and 20 µM polyamine derivative PAM01 hydrochloride solution respectively, wherein pyrogen-free water act as control group, the solution was mixed and incubated at 37° C. for 60 minutes. Murine macrophage RAW 264.7 cell cultured in vitro were transferred into 96-well plates, cell density per well was $1\times10^6$/ml, the volume of medium was 200 µl. 20 µl of above-mentioned mixed solution was added into RAW 264.7 cells, and cell culture supernatant was collected after 12 hours. The levels of inflammatory mediators TNF-α and IL-6 released in each group were detected by ELISA. The steps of ELISA was performed in accordance with the operating manual of mouse ELISA kit of eBioscience Inc, the main steps were: RAW 264.7 cell supernatant was added into ELISA 96-well plate coated with capture antibody, incubated for 2 hours under room temperature, and washed 5 times with PBS. Primary antibody marked with biotin was added and incubated for 1 hour under room temperature, and then washed 5 times with PBS. Horseradish peroxidase marked with avidin was added and incubated for half an hour under room temperature, and then washed 5 times with PBS. Coloring solution was added and incubated for 10 minutes at 37° C., and then stop solution was added. The optical density was measured by microplate reader at 450 nm.

Figure 2A:
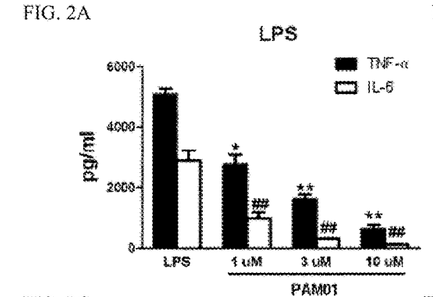
FIG. 2A shows the antagonistic effect on LPS.
Figure 2B:
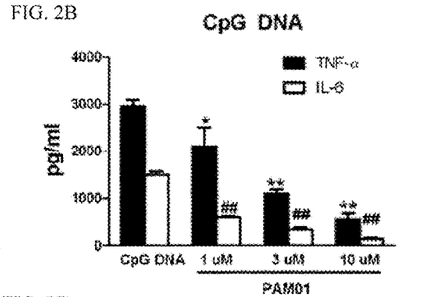
FIG. 2B shows the antagonistic effect on CpG DNA.
Figure 2C:
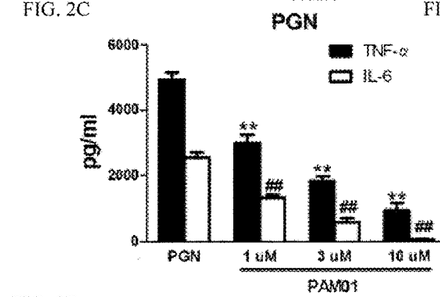
FIG. 2C shows the antagonistic effect on PGN.
Figure 2D:
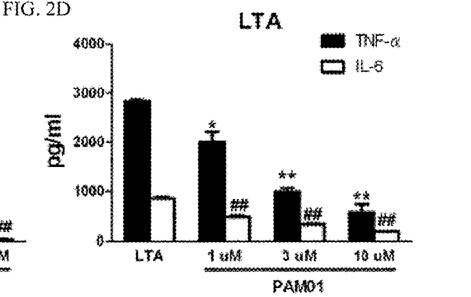
FIG. 2D shows the antagonistic effect on LTA.
Figure 2E:
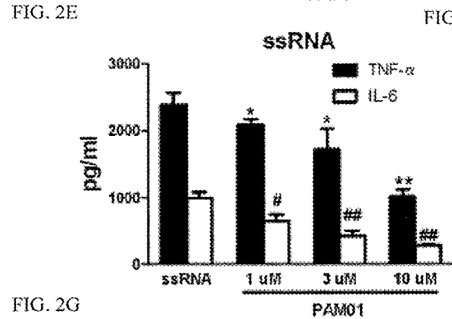
FIG. 2E shows the antagonistic effect on virus ssRNA.
Figure 2F:
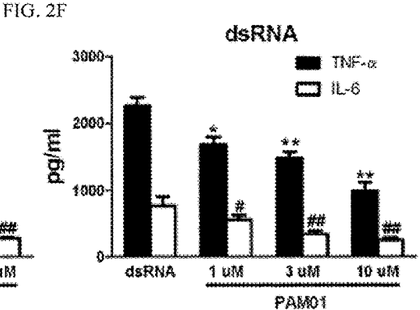
FIG. 2F shows the antagonistic effect on virus dsRNA.
Figure 2G:
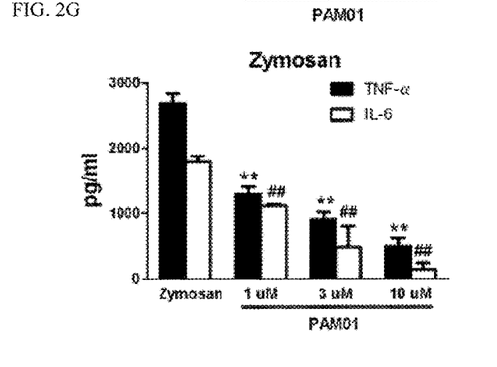
FIG. 2G shows the antagonistic effect on zymosan.

12.2 Experimental result: The stimulation of RAW 264.7 cells with LPS, CpG DNA, PGN, LTA, virus RNA and zymosan could cause obviously increase in TNF-α and IL-6. After treated by polyamine derivative PAM01 hydrochloride, releases of TNF-α and IL-6 reduced significantly (p <0.05 or 0.01) in a dose-dependent manner. Results were shown in FIG. 2, wherein, FIG. 2A shows the antagonistic effect on LPS, FIG. 2B shows the antagonistic effect on CpG DNA, FIG. 2C shows the antagonistic effect on PGN, FIG. 2D shows the antagonistic effect on LTA, FIG. 2E shows the antagonistic effect on virus ssRNA, FIG. 2F shows the antagonistic effect on virus dsRNA, FIG. 2G shows the antagonistic effect on zymosan.

Embodiment 13: Inhibition Effect of Polyamine Derivative PAM01 Hydrochloride on Heat-Killed *Escherichia coli* (Gram Positive Bacteria) and Heat-Killed *Staphylococcus aureus* (Positive Bacteria)-Induced Release of Inflammatory Mediators from Immune Cells 13.1 Experimental method: Bacterial colonies of *Escherichia coli* (EC) or *Staphylococcus aureus* (SA) grown on LB agar plates were picked and transferred to LB liquid culture medium and cultivated at 37° C. until it reached the logarithmic growth phase (10~12 hours). The reactant was centrifuged, the culture medium was removed, and the bacterial precipitation was re-suspended by sterile saline. It was inactivated in boiling water bath for 30 minutes, and the concentration of bacteria was detected. 0.1 ml of the bacteria solution of heat-killed *Escherichia coli* ($1\times10^8$ CFU/ml) or *Staphylococcus aureus* ($5\times10^8$ CFU/ml) prepared with pyrogen-free water were isovolumetricclly mixed with 2, 6 and 20 µM polyamine derivative PAM01 hydrochloride solution respectively, wherein pyrogen-free water act as control group, the solution was mixed and incubated at 37° C. for 60 minutes. Murine macrophage RAW 264.7 cell cultured in vitro were transferred into 96-well plates, cell density per well was $1\times10^6$/ml, the volume of medium was 200 µl. 20 µl of above-mentioned mixed solution was added into RAW 264.7 cells, and cell culture supernatant was collected after 12 hours. The levels of inflammatory mediators TNF-α and IL-6 released in each group were detected by ELISA, which was the same as embodiment 12.

Figure 3A:
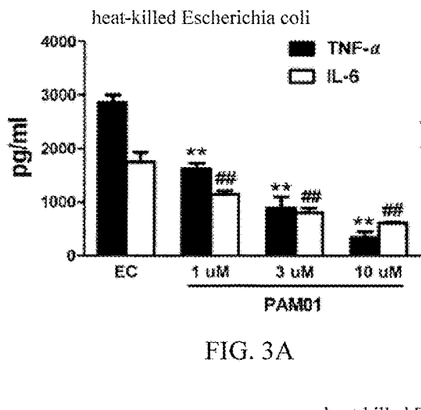
FIG. 3A shows the antagonistic effect on heat-killed *Escherichia coli*.
Figure 3B:
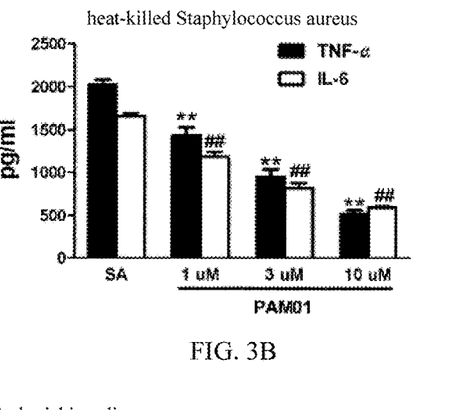
FIG. 3B shows the antagonistic effect on *Staphylococcus aureus*.

13.2 Experimental result: heat-killed *Escherichia coli* bacteria solution and *Staphylococcus aureus* are the representative of gram positive bacteria and gram positive bacteria, each has a mixture of LPS, CpG DNA, PGN, LTA, virus RNA and zymosan, and could induce significant release of TNF-α and IL-6 in RAW264.7 cells. After treated by polyamine derivative PAM01 hydrochloride, the levels of TNF-α and IL-6 reduced significantly, and the levels of TNF-α and IL-6 were significantly reduced as the concentration of polyamine derivative PAM01 hydrochloride increasing (p<0.01), and in a dose-dependent manner. Results were shown in FIG. 3, wherein, FIG. 3A shows the antagonistic effect on heat-killed *Escherichia coli*, FIG. 3B shows the antagonistic effect on heat-killed *Staphylococcus aureus*.

Embodiment 14: Protective Effect of Polyamine Derivative PAM01 Hydrochloride on Mouse Model of Sepsis 14.1 Experimental method: the mouse model of sepsis was challenged by heat-killed *Escherichia coli* (EC) and heat-killed *Staphylococcus aureus* (SA), the detailed operation method was: (1) preparation of heat-killed bacteria solution: same as embodiment 7; (2) animal grouping and modeling: SPF BALB/c mouse (6~8 weeks age, 18~20 g weight) were randomized into model group, low-dose group (0.1 mg/kg) and high-dose group (1 mg/kg), 10 mouse each group, half male and half female. Heat-killed *Escherichia coli* ($1\times10^{10}$ CFU/kg) or *Staphylococcus aureus* ($1\times10^{11}$ CFU/kg) dissolved by normal saline were injected into tail vein for modeling; (3) administration and observation: polyamine derivative PAM01 hydrochloride was dissolved and diluted by normal saline, and injected into tail vein 0, 6, 12 and 24 hours respectively after the injection of bacteria solution, the doses were 0.1 mg/kg (low-dose) and 1 mg/kg (high-dose). The survival rate of animal in 7 days was recorded.

Figure 4A:
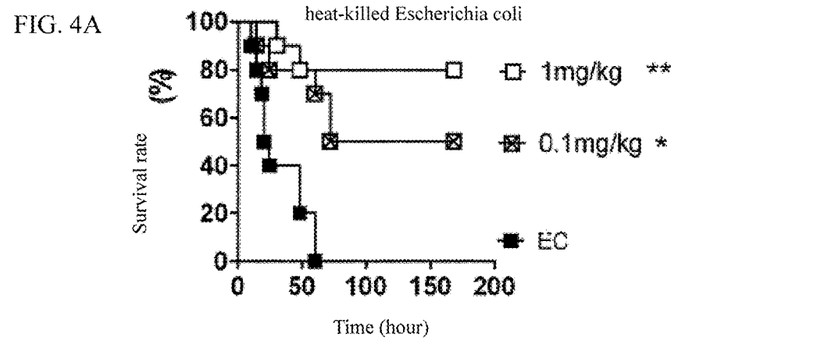
FIG. 4A shows the protection effect on mouse model of sepsis challenged by heat-killed *Escherichia coli*.
Figure 4B:
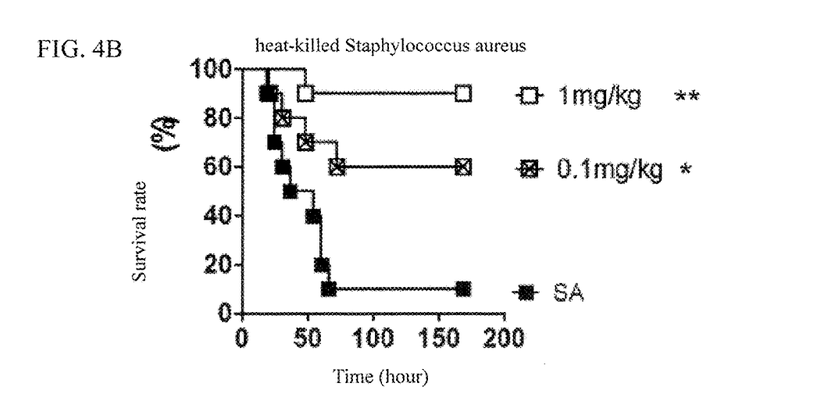
FIG. 4B shows the protection effect on mouse model of sepsis challenged by heat-killed *Staphylococcus aureus*.

14.2 Experimental result: The BALB/c mouse could die after the injection of heat-killed *Escherichia coli* (EC) and heat-killed *Staphylococcus aureus* (SA), the survival rates in 7 days were zero and 10% respectively. In the heat-killed *Escherichia coli*-challenged model, administration with 0.1 and 1 mg/kg of PAM01 hydrochloride could increase the survival rates of model mouse to 50% and 80%. In the heat-killed *Staphylococcus aureus*-challenged model, administration with 0.1 and 1 mg/kg of PAM01 hydrochloride could increase the survival rates of model mouse to 60% and 90%, survival rates are significantly higher than model group (p<0.05 or 0.01), indicating that polyamine derivative PAM01 hydrochloride had a certain protective effect in mouse model of sepsis. Results were shown in FIG. 4, wherein, FIG. 4A shows protective effect on the mouse model of sepsis challenged by heat-killed *Escherichia coli*, FIG. 4B shows protective effect on the mouse model of sepsis challenged by heat-killed *Staphylococcus aureus*.

Embodiment 15: Inhibition Effect of the Sulfate, Phosphate, Mesylate, Benzene Sulfonate and Acetate of Polyamine Derivative PAM01 on LPS, CpG DNA, PGN, LTA, Virus RNA and Zymosan-Induced Release of Inflammatory Mediator from Immune Cells 15.1 Experimental method: experimental method was the same as embodiment 12, except that PAM01 hydrochloride was replaced by PAM01 sulfate, phosphate, mesylate, benzene sulfonate and acetate.

Figure 5A:
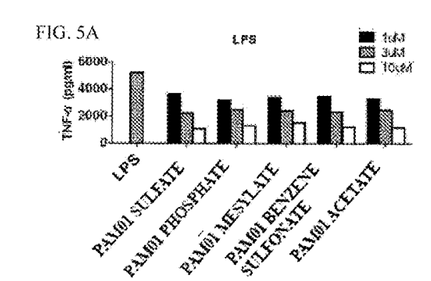
FIG. 5A shows the antagonistic effect on LPS.
Figure 5B:
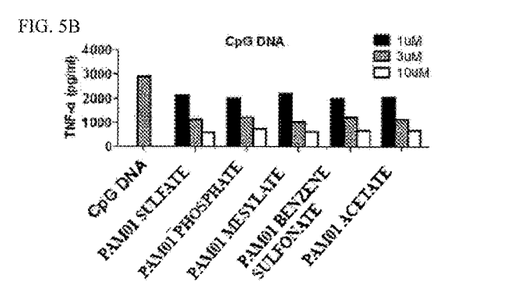
FIG. 5B shows the antagonistic effect on CpG DNA.
Figure 5C:
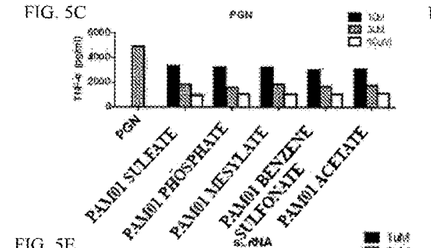
FIG. 5C shows the antagonistic effect on PGN.
Figure 5D:
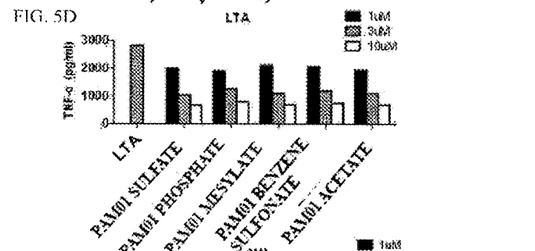
FIG. 5D shows the antagonistic effect on LTA.
Figure 5E:
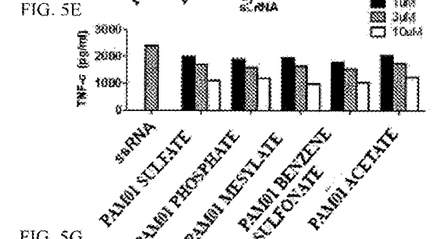
FIG. 5E shows the antagonistic effect on virus ssRNA.
Figure 5F:
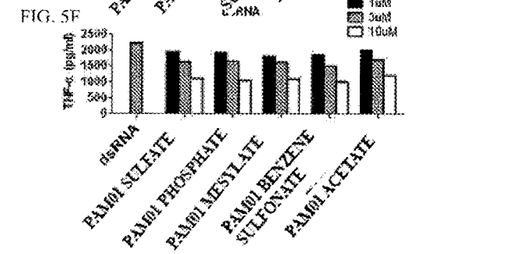
FIG. 5F shows the antagonistic effect on virus dsRNA.
Figure 5G:
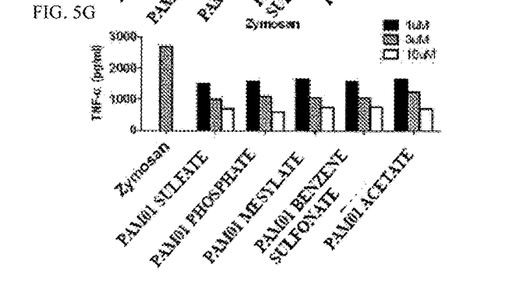
FIG. 5G shows the antagonistic effect on zymosan.

15.2 Experimental result: the sulfate, phosphate, mesylate, benzene sulfonate, acetate of polyamine derivative PAM01 had significant inhibition effect on LPS, CpG DNA, PGN, LTA, virus RNA and zymosan-induced release of inflammatory mediator TNF-α from immune cells (p <0.05 or 0.01). Results were shown in FIG. 5, wherein FIG. 5A shows the antagonistic effect on LPS, FIG. 5B shows the antagonistic effect on CpG DNA; FIG. 5C shows the antagonistic effect on PGN, FIG. 5D shows the antagonistic effect on LTA, FIG. 5E shows the antagonistic effect on virus ssRNA, FIG. 5F shows the antagonistic effect on virus dsRNA, FIG. 5G shows the antagonistic effect on zymosan.

Embodiment 16: Inhibition Effect of Polyamine Derivative PAM02~06 Hydrochloride on LPS, CpG DNA, PGN, LTA, Virus RNA and Zymosan-Induced Release of Inflammatory Mediator from Immune Cells

16.1 Experimental method: experimental method was the same as embodiment 12, except that PAM01 hydrochloride was replaced by PAM02~06 hydrochloride.

Figure 6A:
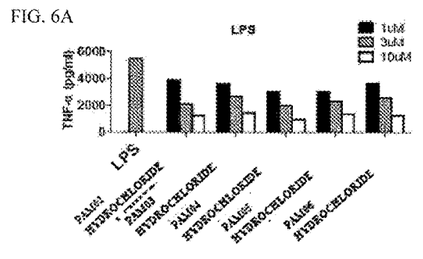
FIG. 6A shows the antagonistic effect on LPS.
Figure 6B:
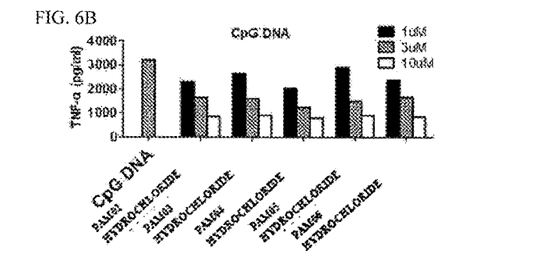
FIG. 6B shows the antagonistic effect on CpG DNA.
Figure 6C:
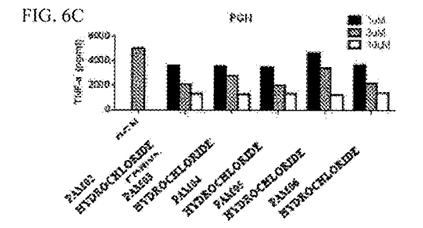
FIG. 6C shows the antagonistic effect on PGN.
Figure 6D:
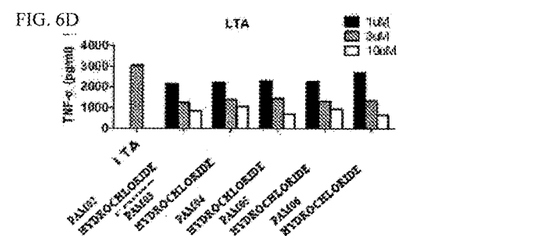
FIG. 6D shows the antagonistic effect on LTA.
Figure 6E:
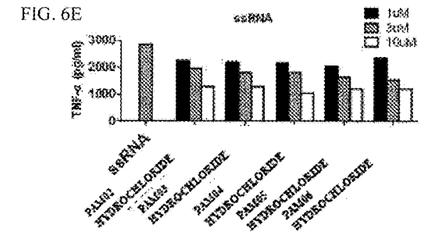
FIG. 6E shows the antagonistic effect on virus ssRNA.
Figure 6F:
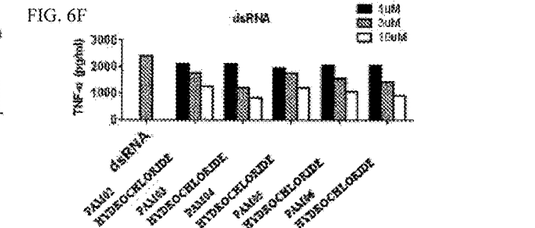
FIG. 6F shows the antagonistic effect on virus dsRNA.
Figure 6G:
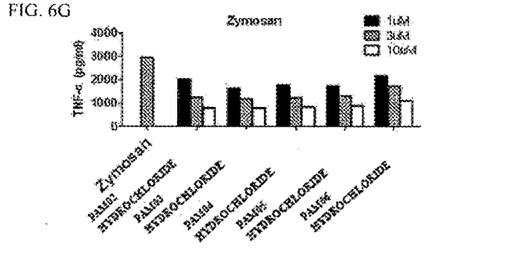
FIG. 6G shows the antagonistic effect on zymosan.

16.2 Experimental result: polyamine derivative PAM02~06 hydrochloride had significant inhibition effect on LPS, CpG DNA, PGN, LTA, virus RNA and zymosan-induced release of inflammatory mediator TNF-α from immune cells (p <0.05 or 0.01). Results were shown in FIG. 6, wherein, FIG. 6A shows the antagonistic effect on LPS, FIG. 6B shows the antagonistic effect on CpG DNA; FIG. 6C shows the antagonistic effect on PGN, FIG. 6D shows the antagonistic effect on LTA, FIG. 6E shows the antagonistic effect on virus ssRNA, FIG. 6F shows the antagonistic effect on virus dsRNA, FIG. 6G shows the antagonistic effect on zymosan.

Above-mentioned experiments showed that medicinal salts of polyamine derivatives of the present invention have significant antagonistic effects on LPS, CpG DNA, PGN, LTA, virus RNA and zymosan, and was capable of inhibiting inflammatory mediator release from immune cells induced by these molecules, whereby increasing the survival rate of animal model of sepsis and suitable for the treatment of sepsis.

The invention claimed is:

1. The medicinal salts of polyamine derivatives, wherein the medicinal salts are salts formed with polyamine derivatives shown in general formula 1 and pharmaceutically acceptable acids through chemical combination, the polyamine derivatives have structure of general formula 1:

Wherein, $R_1$~$R_5$ are selected from H or OH or $OCH_3$; $n_1$~$n_5$ are any integer between 0~10.

2. The medicinal salts of polyamine derivatives according to claim 1, wherein $n_1$~$n_4$ are any integer between 1~10; $n_5$ is any integer between 0~10.

3. The medicinal salts of polyamine derivatives according to claim 1, wherein the pharmaceutically acceptable acid is an inorganic acid or an organic acid.

4. The medicinal salts of polyamine derivatives according to claim 2, wherein the inorganic acid is hydrochloric acid, sulfuric acid, phosphoric acid or nitric acid; the organic acid is acetic acid, oxalic acid, propanedioic acid, succinic acid, benzoic acid, trifluoroacetic acid, maleic acid, fumaric acid, citric acid, tartaric acid, methanesulfonic acid, benzenesulfonic acid or p-Toluene sulfonic acid.

5. A preparation method of the medicinal salts of polyamine derivatives, comprising following steps:

Wherein, A is a pharmaceutically acceptable acid;
1) In dichloromethane solution, compound I reacts with protective agent di-tert-butyl dicarbonate to generate compound II, the equivalent ratio of the compound I and the di-tert-butyl dicarbonate is 1:0.5~2;
2) In a saturated solution of ammonia in methanol, the compound III is generated from compound II through hydrogenation;
3) In ethanol or methanol solution, the compound III reacts with α,β-unsaturated nitrile to generate compound IV, the equivalent ratio of the compound III and the α,β-unsaturated nitrile is 1:2~1:3;
4) In a mixed solution of dichloromethane and N,N-Dimethylformamide, compound V reacts with carboxyl activator chlorinated sulfoxide to generate compound VI, the equivalent ratio of the compound V and the carboxyl activator is 1:1~1:2;
5) In a mixed solution of dichloromethane and triethylamine, compound IV reacts with compound VI to generate compound VII, the equivalent ratio of the compound IV and compound VI is 1:2~1:3;
6) In a saturated solution of ammonia in methanol, compound VIII is generated from compound VII through hydrogenation;
7) In methanol solution or a mixed solution of methanol, tetrahydrofuran and water, the medicinal salt of the compound shown in general formula 1 is generated from compound VIII through catalytic hydrogenation under the existence of acid, the volume ratio of the methanol, tetrahydrofuran and water is 3:1:1, the equivalent ratio of the compound VIII and the acid is 1:1~1:8.

6. The method according to claim 5, wherein the reaction conditions of step 2) and 6) include using raney nickel corresponding to 10~50% of the mass of the compound VII, the pressure is 1~10 Mpa.

7. The method according to claim 5, wherein the reaction condition of step 7) includes using palladium on carbon corresponding to 10~30% of the mass of the compound VIII, the pressure ranges from atmospheric pressure to 10 Mpa.

8. The medicinal salts of polyamine derivatives according to claim 2, wherein the inorganic acid is hydrochloric acid or sulfuric acid.

9. The medicinal salts of polyamine derivatives according to claim 2, wherein the organic acid is acetic acid, propanedioic acid, succinic acid, maleic acid, fumaric acid, citric acid, methanesulfonic acid, benzenesulfonic acid or p-Toluene sulfonic acid.

* * * * *